United States Patent [19]

Gavlin et al.

[11] 4,316,846

[45] Feb. 23, 1982

[54] RECOVERY OF APROTIC AMIDES

[75] Inventors: Gilbert Gavlin, Lincolnwood; Romas Cesas, Chicago, both of Ill.

[73] Assignee: Custom Organics, Inc., Chicago, Ill.

[21] Appl. No.: 908,275

[22] Filed: May 22, 1978

Related U.S. Application Data

[63] Continuation-in-part of Ser. No. 763,868, Jan. 31, 1977, abandoned.

[51] Int. Cl.$^3$ ............... C07C 103/127; C07C 103/34; C07C 103/36; C07D 207/06
[52] U.S. Cl. ............................. 260/326.45; 564/216
[58] Field of Search ...................... 260/326.45, 561 R; 564/216

[56] References Cited

U.S. PATENT DOCUMENTS

| | | | |
|---|---|---|---|
| 3,959,371 | 5/1976 | Gaulin et al. | 260/561 R |
| 4,013,640 | 3/1977 | Somekh | 260/561 R X |

OTHER PUBLICATIONS

Kuroda et al., CA 79: 105073k, (1973).
Kuroda et al., CA 82: 170665f, (1975).
Suzuki et al., CA 83: 178374b, (1975).
Kozai et al., CA 83: 29716n, (1975).
CRC Handbook of Chem. & Physics, 48th Ed., Weast, pp. C-79, C-327, C-407 and C-527, (1967).
Drago et al., CA 81: 30473w, (1974).
Seliverotov, CA 73: 81270v, (1970).

*Primary Examiner*—Thomas A. Waltz
*Attorney, Agent, or Firm*—John L. Hutchinson

[57] ABSTRACT

The present invention relates to the recovery of three aprotic amide solvents from their water solutions by extraction with a selected class of organic solvents characterized generally by having two electron withdrawing substituents, exemplified by fluorine and chlorine, located on a carbon atom which also contains a hydrogen atom.

6 Claims, No Drawings

RECOVERY OF APROTIC AMIDES

THE INVENTION

The present application is a continuation-in-part of our application Ser. No. 763,868 filed Jan. 31, 1977 now abandoned.

N,N-dimethylacetamide, N,N-dimethylformamide and N-methyl-2-pyrrolidone are sometimes referred to as aprotic solvents. Such compounds are highly polar, do not have an available proton for hydrogen bond formation and are compatible with many organic and inorganic substances. They are good ionizing solvents and accelerate reactions producing ions. In view of their unique solvent characteristics for both inorganic and organic substances they have become substantially irreplaceable in the synthesis of various commercially important organic chemicals. However, they are expensive and must be recovered in high purity for recycling.

The above aprotic amides are completely miscible with water and are strongly hygroscopic and, accordingly, can be readily separated from reaction mixtures by washing with water. Also, such solvents can be removed from gas streams by washing with water. Hence, their recovery for recycling will normally be from dilute water solution.

In general, recovery of the amides in accordance with the present invention will involve initial dilute water solutions wherein the water comprises between about 25% to 90% by weight of the solution, although most initial solutions to be extracted will usually contain between about 45% to 90% by weight of water. Such solutions may sometimes contain a soluble salt, such as calcium chloride or alkali acetate, in an amount up to a maximum of about 25 % by weight based on the weight of water. The amount of salt present throughout the hereinafter described extraction process is in a range such that it has no effect on the extraction contemplated, as would be the case in certain "salting out" solvent recovery processes. Some initial aqueous amide solutions will frequently contain about 10–15 percent by weight of amide, 85–90 percent by weight of water and from about 2–15 percent by weight of a soluble salt, such as calcium chloride or sodium or potassium acetate, based on the weight of water.

All three of the aprotic amides are weakly basic and form complexes of varying strength with acidic materials. The base strength, $pK_{BH+}$, for N-methylpyrrolidone has been reported to be 0.92 at 25° C. High boiling azeotropes of the aprotic amides, representing strong association, are known, exemplified by the following:
N-methylpyrrolidone: propionic acid
dimethylacetamide: acetic acid
dimethylformamide: formic acid The extreme difficulty of separating dimethylacetamide from acetic acid by azeotropic distillation with a third solvent is disclosed in U.S. Pat. No. 3,959,371.

It is possible to remove water from solution of the three aprotic amides by fractional distillation, however, from a commercial viewpoint such a separation is not practical due to the investment in equipment and energy required. Equipment size for distillation separation is an inverse function of molecular weight and water with a molecular weight of 18 is one of the lowest molecular weight materials boiling at 100° C. Also the latent heat of vaporization of water of about 1000 Btu/lb is about five times that of the average organic compound. Accordingly, with the accelerating cost of energy and equipment, an alternate to the separation of the aprotic amides from water by fractional distillation is desirable.

A special class of compounds have been discovered which are unusually effective as extractants for aprotic amides from dilute water solutions such as are encountered in spent solvents from various commercial operations. The effectiveness of this special class of compounds as extractants is especially surprising in view of the high affinity for water of the aprotic amides. The water affinity problem is discussed in the aforementioned U.S. Pat. No. 3,959,371 involving the separation of acetic acid from dimethylacetamide wherein, after neutralization with potassium hydroxide, it is necessary to decrease the water constant by fractional distillation prior to extraction of the amide with xylene. The new class of solvent compounds may be generally characterized as those which are liquid with a boiling point between 40°–110° C., have low water solubility, are readily separable from the aprotic amides by distillation and have either two or three electron withdrawing substituents located on carbon atoms also containing available hydrogen. More specifically, the solvent compounds contemplated by the present invention are represented by the following general formula

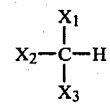

wherein $X_1$ and $X_2$ are from the class consisting of —Cl, —CH$_2$Cl, —CHCl$_2$, —CHClF, —CHF$_2$, —CFCl$_2$, —CF$_2$Cl, —CF$_3$, —CHClR, —CCl$_2$R, —CClFR, —CF$_2$R;
wherein R is from the class consisting of —CH$_3$, —C$_2$H$_5$ and —C$_3$H$_7$ and
wherein $X_3$ is from the class consisting of $X_1$, $X_2$, R and H.

The particular solvents contemplated for use in recovering the aprotic amides are further characterized by having a partition coefficient K which will permit a substantially 95% extraction from dilute water solutions as described in approximately four to six extraction stages using substantially equal volumes of solvent and the water solution of amide in each stage. The stages required will normally depend on the quantity of amide present in the initial solution and the particular solvent used. Extractions with the present aprotic amides may be compared to analogous extractions with more common solvents, such as toluene, xylene, trichloroethylene or chlorobenzene wherein from about 10–30 or more extraction stages would be required to achieve 95% extraction.

The partition coefficient is defined as $$K = (Ce/Cr)$$

where C represents the concentration of aprotic amide in grams/100 ml solvent, e designates the extract phase and r the raffinate phase.

Preferred solvents are chloroform; methylene chloride; 1,2-dichloroethane and 1,2-dichloro-1-fluoro ethane due to the fact that they have been found to have the highest partition coefficients of all solvents tested to date. In general the partition coefficient, as defined above, should be a minimum of about 0.60 to achieve effective commercial results.

In order to further illustrate the principles of the invention, the following examples are presented using dimethylacetamide as an exemplary aprotic amide to be extracted from a water solution. The sample solutions include neutralized acetic acid to represent similar solutions frequently encountered in spent commercial solvent solutions.

EXAMPLE 1

A dilute solution of dimethylacetamide having the following composition was prepared:
dimethylacetamide:50 g
potassium acetate:15 g
water:50 g Using 50 ml of the above test solution 50 ml portions of the following solvents were used in a series of extraction runs as indicated:

| Solvent | First Stage Extract Volume (ml) | (K) Partition Coefficient | Stages For 95% Extraction |
|---|---|---|---|
| $CH_2Cl_2$ | 80 | 1.26 | 4 |
| $CHClFCH_2Cl$ | 76 | 1.00 | 5 |
| $CHCl_3$ | 75 | .98 | 5 |
| $CH_2ClCH_2Cl$ | 74 | .81 | 5 |
| Chlorobenzene | 60 | .25 | 14 |
| $CCl_2=CHCl$ | 60 | .25 | 14 |
| $CCl_4$ | 54 | .09 | — |

In general it has been found that solvents with a single halogen atom and having unsaturation are substantially ineffective or impractical for use in the extraction process.

EXAMPLE 2

An aqueous solution was prepared having the following composition:
dimethylacetamide:100 g
water:100 g
potassium acetate:30 g 100 ml of the above solution were shaken in a separatory funnel in four successive extraction steps with 100 ml portions of chloroform, the respective layers formed in each extraction step being separated by decanting. After the last treatment, the water layer contained less than one gram of dimethylacetamide as determined by gas chromatography.

The four chloroform extracts were combined and subjected to simple distillation. After the pot temperature had reached 120° C., approximately 375 ml of chloroform had been obtained as distillates. At this point 25 ml of toluene were added to the pot for assistance in removing the last traces of chloroform during final distillation and the contents transferred to a distillation column. The remainder of the chloroform was then fractionally distilled off. The pressure was reduced to 200 mm Hg and the fractional distillation continued. The following four fractions were obtained:

|   |   | b.p.°C. | wt. g. |
|---|---|---|---|
| 1 | toluene | 70 | 15 |
| 2 | intermediate | 70–125 | 10 |
| 3 | dimethylacetamide | 12.5 | 80 |
| 4 | residue |   | 10 |

Fractions 2, 3 and 4 represent a recovery of 95 grams of the dimethylacetamide. In a commercial process fractions 2 and 4 would be recycled.

While the above examples disclose extractions on a batch basis for purposes of illustration, the principles and ratios of the present invention are likewise applicable to and are intended for use in continuous or substantially continuous extraction processes and, particularly, the type of substantially continuous process known as cross current extraction.

Having described the invention the same is only intended to be limited by the following claims.

We claim:

1. In a process for extracting substantially 95% of an aprotic amide from the class consisting of N,N-dimethylacetamide, N,N-dimethylformamide and N-methyl-2-pyrrolidone from a dilute aqueous solution containing the aprotic amide and water, said dilute aqueous solution containing water in the initial amount of between about 25–90 percent by weight and a maximum of about 25% by weight based on the weight of water of a soluble salt, which process consists essentially of subjecting the dilute aqueous solution to approximately four to six successive extraction steps with substantially equal volume of an organic solvent compound having the following formula

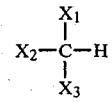

wherein $X_1$ and $X_2$ are from the class consisting of —Cl, —$CH_2Cl$, —$CHCl_2$, —CHClF, —$CHF_2$, —$CFCl_2$, $CF_2Cl$, —$CF_3$, —CHClR, —$CCl_2R$, —CClFR, —$CF_2R$;

wherein R is from the class consisting of —$CH_3$, —$C_2H_5$ and —$C_3H_7$ and wherein $X_3$ is from the class consisting of $X_1$, $X_2$, R and H, permitting the mixture of organic solvent and aqueous solution in each extraction step to separate into an aqueous phase and an organic solvent phase containing extracted aprotic amide and separating the organic solvent phase from the aqueous phase.

2. A process as described in claim 1 wherein said organic solvent compound is chloroform.

3. A process as described in claim 1 wherein said organic solvent compound is methylene chloride.

4. A process as described in claim 1 wherein said organic solvent compound is 1,2 dichloroethane.

5. A process as described in claim 1 wherein said organic solvent compound is 1,2 dichloro, 1 fluoro ethane.

6. A process as described in claim 1 wherein the initial water content is present between 45 to 90 percent by weight.